United States Patent

Crawley

Patent Number: 5,210,209
Date of Patent: May 11, 1993

[54] PYRAZOLO(1,5-A)BENZIMIDAZOLE COUPLERS

[75] Inventor: Michael W. Crawley, Kingwood-Watford, United Kingdom

[73] Assignee: Eastman Kodak Company, Rochester, N.Y.

[21] Appl. No.: 678,288

[22] PCT Filed: Aug. 1, 1990

[86] PCT No.: PCT/GB90/01192
§ 371 Date: Jun. 3, 1991
§ 102(e) Date: Jun. 3, 1991

[87] PCT Pub. No.: WO91/01984
PCT Pub. Date: Feb. 21, 1991

[30] Foreign Application Priority Data
Aug. 4, 1989 [GB] United Kingdom ............ 8917918

[51] Int. Cl.$^5$ .......................................... C07D 487/04
[52] U.S. Cl. .................................. 548/302.1; 544/9; 540/498; 540/554
[58] Field of Search .................. 548/324, 302.1

[56] References Cited

U.S. PATENT DOCUMENTS 3,061,432 10/1962 Menzel et al. .................. 96/55
3,189,616 6/1965 Loffler et al. ................. 260/309.2
3,369,897 2/1968 Menzel et al. ................. 96/56.5

FOREIGN PATENT DOCUMENTS 61-18949 1/1986 Japan .

OTHER PUBLICATIONS

Chemical Abstracts, vol. 102, entry 102:80263a, 1985.
Chemical Abstracts, vol. 96, entry 96:124509z, 1982.
Chemical Abstracts, vol. 95, entry 95:117074e, 1981.
Chemical Abstracts, vol. 87, entry 87:76356n, 1977.
Chemical Abstracts, vol. 110, entry 110:125210q, 1989.
Chemical Abstracts, vol. 63, entry 4440h, 1965.
Monatshefte, fur Chemi, 114, 425–432, 1983.
Chemical Abstracts 96:204546n, vol. 96, 1982.
Chemical Abstracts 86 (11): 72584s (J. Org. Chem., 42(3), 542–5,) 1977.
Chemical Abstracts 101(9): 72703j (Khim. Geterotsikl. Soedin., (5), 700–1, 1984.
Heterocycles, vol. 6, No. 7, 979–981, 1977.

Primary Examiner—Mary C. Lee
Assistant Examiner—Lenora A. Miltenberger
Attorney, Agent, or Firm—Arthur E. Kluegel

[57] ABSTRACT

The invention provides a method for the production of a pyrazolo(1,5-a)benzimidazole of the general formula (A):

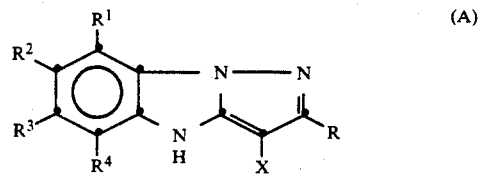

wherein
R is a substituted or unsubstituted alkyl or aryl group, and
$R^1$–$R^4$ = R, H, halogen, OR, COOR, CONHR, $SO_2$, $NO_2$ NHR, $NR_2$, or CN, and
X is hydogen or a reactive group releasable on coupling with an oxidized color developer, wherein the invention provides reacting a 2-amino or 2-mercapto substituted benzimidazole to form a triazepinone or a thiadiazino derivative respectively, ring contracting said triazepinone or thiadiazino derivative to give the corresponding 2-methylpyrazolobenzimidazole product, and subsequently removing the substituents at the -3 or -4 positions to provide a compound of the general formula (1).

5 Claims, No Drawings

PYRAZOLO(1,5-A)BENZIMIDAZOLE COUPLERS

DESCRIPTION

The present invention relates to pyrazolo(1,5-a)benzimidazole couplers.

The pyrazolo(1,5-a)benzimidazole (PBI) couplers are useful as magenta couplers for colour photography.

Although previous synthetic routes for the production of these compounds are known the present invention provides a method for their production using ring closure reactions of benzimidazole derivatives.

According to the present invention there is provided a method for the production of a pyrazolo(1,5-a)benzimidazole of the general formula (A):

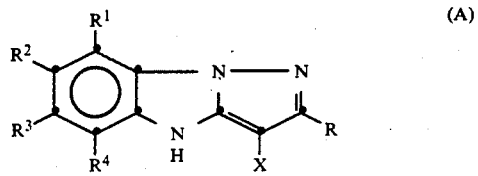

wherein
R is a substituted or unsubstituted alkyl or aryl group, and
$R^1$-$R^4$=R, H, halogen, OR, COOR, CONHR, $SO_2$, $NO_2$ NHR, $NR_2$, or CN, and
X is hydrogen or a group releasable on coupling with an oxidised colour developer, which method is characterised by reacting a 2-amino or 2-mercapto substituted benzimidazole to form a triazepinone or a thiadiazino derivative respectively, ring contracting said triazepinone or thiadiazino derivative to give the corresponding pyrazolobenzimidazole product, and subsequently removing the substituents at the -3 or -4 positions to provide a compound of the general formula (A).

In a preferred form of the invention R is a methyl or phenyl group and $R^1$ to $R^4$ are all H. In another form of the invention R, $R^2$ and $R^3$ are all methyl with $R^1$ and $R^4$ respectively being a hydrogen substituent.

In one preferred form of the invention the 2-aminobenzimidazole starting material is formed into a 1,2,4-triazepinone derivative and subsequently subjected to ring contraction of the 7-member ring to the pyrazole form.

In another form of the invention a thiadiazinobenzimidazole derivative is subjected to a ring contraction of the 6-member ring to give the pyrazole form.

Accordingly the alkyl or aryl pyrazolo(1,5-a)benzimidazole derivatives of the present invention may be formed either by means of the mercapto compound (referred to hereinafter as the sulphur extrusion route), or by means of the amino substituted compound (hereinafter referred to as the ring contraction route).

In one generally exemplary exposition of the sulphur extrusion route the starting materials are selected from a 2-mercaptobenzimidazole and an α-haloketone.

The former compounds are readily available from ortho-phenylene diamines and carbon disulphide.

Accordingly 2-methylpyrazolo(1,5-a)benzimidazole may be produced by reacting 2-mercaptobenzimidazole (1) with a haloketone such as chloroacetone at the sulphur atom to give a corresponding substituted ketone (2). A plurality of different α-haloketones may be utilized in this reaction depending upon the desired product or reaction conditions.

Thus where a 2-mercaptobenzimidazole is utilized the substituted ketone starting material may be 2-(acetylmethylthio)benzimidazole. If this last product is reacted under alkaline aqueous conditions with hydroxylamine O-sulphonic acid, at for example, room temperature it gives a precipitate of a thiadiazinobenzimidazole derivative (4) in high yield. This last reaction is believed to proceed via the N-amination of the 2-(acetylmethylthio)benzimidazole to give an intermediate product designated (3) which rapidly cyclises with a loss of water to give the desired compound.

The six membered ring including the sulphur atom may be ring contracted by heating with a mixture of acetic acid and toluene for a number of hours; for example 80. The product which may be 4-acetyl-3-acetylthio-2-methylpyrazolo(1,5-a)-benzimidazole (5) may then be desulphurised under reflux in the presence of mineral acid and ethanol to give the desired 2-methylpyrazolobenzimidazole product.

This reaction sequence is shown diagrammatically in scheme 1 below.

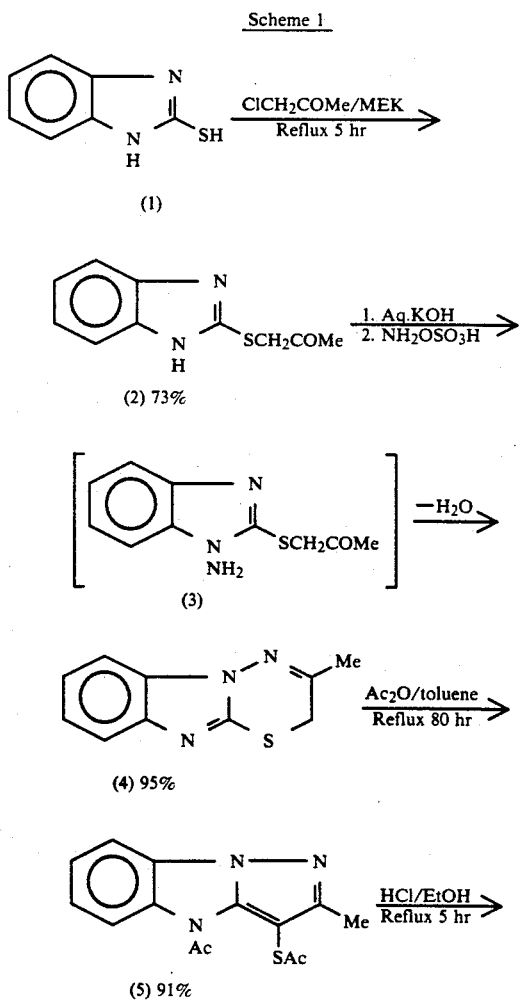

-continued
Scheme 1

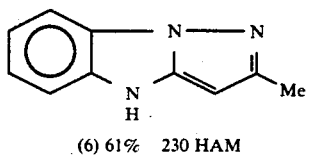

(6) 61%  230 HAM

The mechanism of the ring contraction of scheme 1 has not yet been fully elucidated. It is thought probable that a mechanism somewhat as shown in scheme 2 below is involved. Without limitation it is believed that the arrangement shown in scheme 2 involves the initial acylation of the imidazole nitrogen followed by ring formation and subsequent cleavage, possibly assisted by the generation of an acetate anion. A similar mechanism could exist whereby the sulphur atom is initially acylated; the penultimate structure is common to both mechanisms.

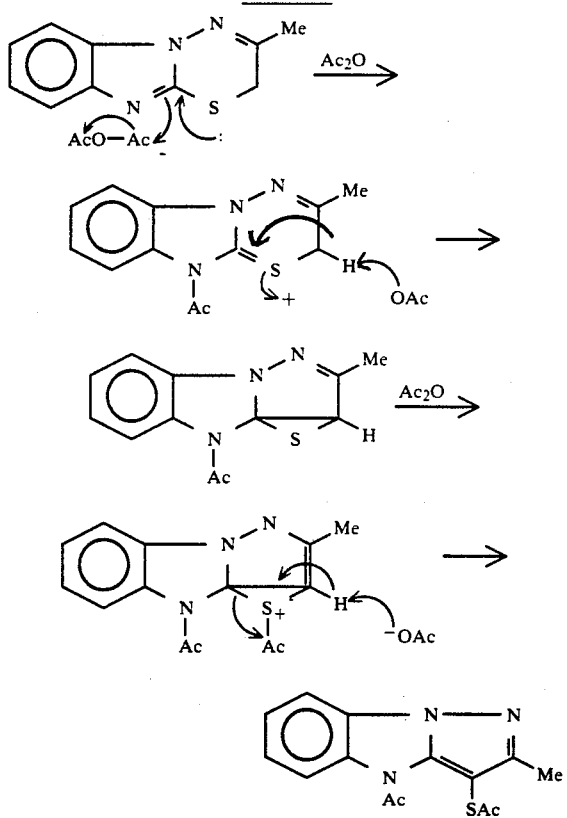

Scheme 2

The particular advantages of this route, are that clean, high yielding steps provide the target compound; starting from starting materials which are readily available.

In the ring contraction route alluded to above, a seven membered 1,2,4-triazepinone derivative of the pyrazole ring of the coupler is made by heating in the absence or in the presence of acetic anhydride. Starting materials for the production of PBI by this route may include 2-amino-benzimidazole. This compound is readily available from a number of sources usually via ortho-phenylenediamine or a 2-H-benzimidazole. If the 2-methyl derivative is to be the final product, 2-aminobenzimidazole may be the starting material. In this case the starting material may be reacted in alkaline solution with hydroxylamine O-sulphonic acid to give a 1,2-diaminobenzimidazole intermediate. This intermediate may be reacted with alkyl acetoacetate in an organic solvent, for example xylene containing acetic acid, to give a 1,2,4-triazepinone derivative. This seven-membered ring structure may be ring contracted by reflux, in the presence of acetic anhydride for example, to afford two products in approximate equal quantities; the first being a diacetyltriazepinone and the second being N-acetyl-2-methylpyrazolobenzimidazole. Reflux in the presence of acidified alcohol removes the acetyl component to provide the target compound.

This reaction sequence is demonstrated diagrammatically in scheme 3 below.

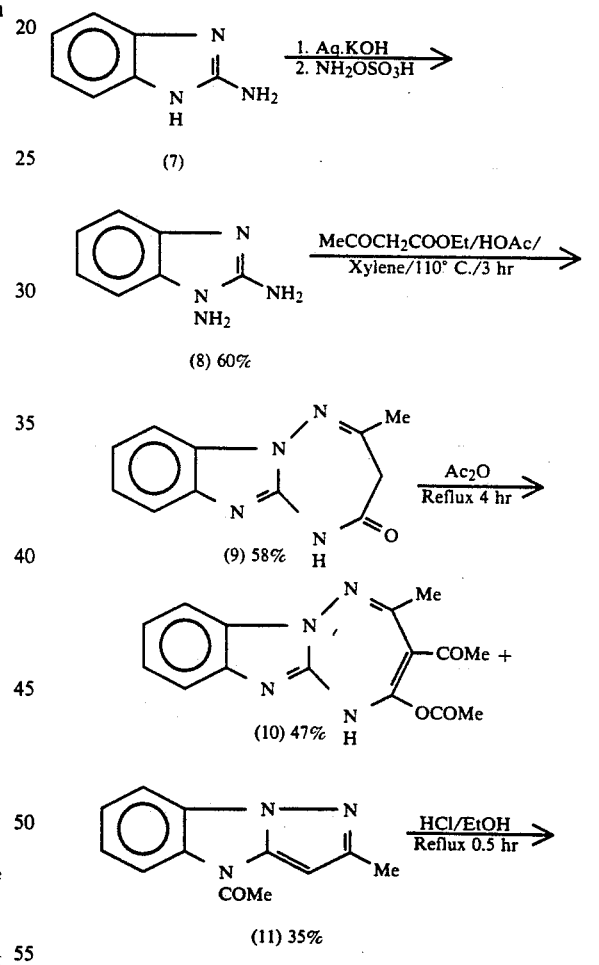

Although the mechanism of the ring contraction step has yet to be fully elucidated, and we do not wish to be held to any precise theory thereof, the pathway seems to be the same as for the sulphur extrusion method. In this case the intramolecular cyclisation occurs to give a four rather than a three membered ring with subsequent loss of an isocyanate anion.

Scheme 4

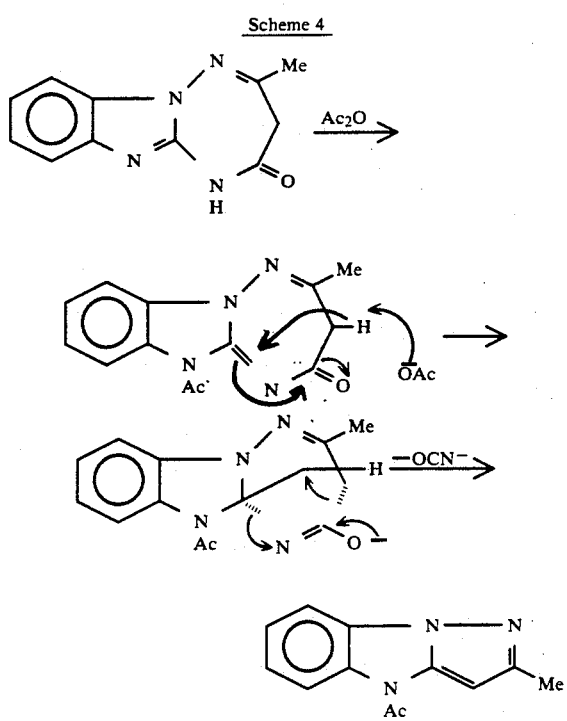

This last route has also been applied to the synthesis of 2,6,7-trimethylpyrazolo(1,5-a)benzimidazole from 4,5-dimethyl-benzimidazole. This product has been more difficult to produce because of the difficulties of providing suitable starting materials in the prior art.

In order to provide this last compound the 4,5-dimethylbenzimidazole was N-aminated to give a 91% crude product which gave an 81% yield of the corresponding triazepinone with an alkyl acetoacetate. This product was then refluxed with acetic anhydride to give the same mixture of products, one corresponding to the diacetyl derivative of the triazepinone (12%) yield and the other to give N-acetyl PBI at 54% yield; hydrolysis of the latter with hydrochloric acid in an alcohol such as ethanol gave free PBI at 98% yield.

The ring contraction route in accordance with the present invention is useful in the preparation of novel PBIs with substituents in the benzo ring which are normally difficult to prepare.

By analogous methods the 2-methylpyrazolo-(1,5-a)-dimethylbenzimidazole and the 2-phenylpyrazolo (1,5-a)benzimidazole derivatives shown can be obtained.

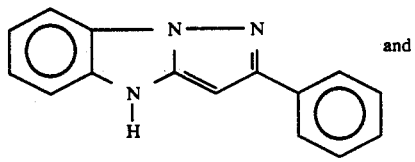 and

-continued

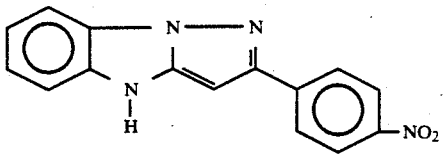

The dye-forming couplers of this invention can be used in the ways and for the purposes that dye-forming couplers have been previously used in the photographic art. They may be dissolved in processing solutions (unballasted) or incorporated into photographic materials (normally ballasted).

Typically, the couplers are incorporated in silver halide emulsions and the emulsions coated on a support to form a photographic element. Alternatively, the couplers can be incorporated in photographic elements adjacent the silver halide emulsion where, during development, the coupler will be in reactive association with development products such as oxidized colour developing agent. Thus, as used herein, the term "associated therewith" signifies that the coupler is in the silver halide emulsion layer or in an adjacent location where, during processing, it will come into reactive association with silver halide development products.

The photographic elements can be single colour elements or multicolour elements. In a multicolour element, the magenta dye-forming couplers of this invention would usually be associated with a green-sensitive emulsion, although they could be associated with an emulsion sensitized to a different region of the spectrum, or with a panchromatically sensitized ortho-chromatically sensitized or unsensitized emulsion. Multicolour elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art.

A typical multicolour photographic element would comprise a support bearing a magenta dye image-forming unit comprised of at least one green-sensitive silver halide emulsion layer having associated therewith at least one magenta dye-forming coupler, at least one of the magenta dye-forming couplers being a coupler of this invention, and yellow and cyan dye image-forming units comprising at least one blue- or red-sensitive silver halide emulsion layer having associated therewith at least one yellow or cyan dye-forming coupler respectively. The element can contain additional layers, such as filter layers.

In the following discussion of suitable materials for use in the emulsions and elements of this invention, reference will be made to Research Disclosure, December 1978, Item 17643, published by Industrial Opportunities Ltd., The Old Harbourmaster's, 8 North Street, Emsworth, Hants P010 7DD, U.K. This publication will be identified hereafter as "Research Disclosure".

The silver halide emulsion employed in the elements of this invention can be either negative-working or positive-working. Suitable emulsions and their preparations are described in Research Disclosure Sections I and II and the publications cited therein. Suitable vehicles for the emulsion layers and other layers of elements of this invention are described in Research Disclosure Section IX and the publications cited therein.

In addition to the couplers of this invention, the elements of the invention can include additional couplers as described in Research Disclosure Section VII, paragraphs D, E, F and G and the publications cited therein. The couplers of this invention and any additional couplers can be incorporated in the elements and emulsions as described in Research Disclosures of Section VII, paragraph C and the publications cited therein.

The photographic elements of this invention or individual layers thereof, can contain brighteners (see Research Disclosure Section V), antifoggants and stabilizers (see Research Disclosure Section VI), antistain agents and image dye stabilizer (see Research Disclosure Section VII, paragraphs I and J), light absorbing and scattering materials (see Research Disclosure Section VIII), hardeners (see Research Disclosure Section XI), plasticizers and lubricants (see Research Disclosure Section XII), antistatic agents (see Research Disclosure Section XIII), matting agents (see Research Disclosure Section XVI) and development modifiers (see Research Disclosure Section XXI).

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a colour developing agent to reduce developable silver halide and oxidize the colour developing agent. Oxidized colour developing agent in turn reacts with the coupler to yield a dye.

Preferred colour developing agents are p-phenylene diamines. Especially preferred are 4-amino-N,N-diethylaniline hydrochloride, 4-amino-3-methyl-N-ethyl-N-$\beta$-(methanesulfonamideo)ethylaniline sulphate hydrate, 4-amino-3-methyl-N-ethyl-N-$\beta$-hydroxyethylaniline sulphate, 4-amino-3-$\beta$-(methanesulfonamido)ethyl-N,N-diethylaniline hydrochloride and 4-amino-N-ethyl-N-(2-methoxyethyl)-m-toluidine di-p-toluene sulfonate.

With negative-working silver halide emulsions this processing step leads to a negative image. To obtain a positive (or reversal) image, this step can be preceded by development with a non-chromogenic developing agent to develop exposed silver halide, but not form dye, and then uniform fogging of the element to render unexposed silver halide developable. Alternatively a direct positive emulsion can be employed to obtain a positive image.

Development is followed by the conventional steps of bleaching, fixing or bleach-fixing, to remove silver and silver halide, washing and drying.

The invention will now be described, by way of illustration only in the following examples of the invention.

EXAMPLE 1 a) The Sulphur Extrusion Route

Preparation of 2-(Acetylmethylthio)benzimidazole (2)

2-Mercaptobenzimidazole (14.6 g, 0.1 mole) and chloroacetone (9.25 g, 0.1 mole) were added to 2-butanone (400 ml) and refluxed for 5 hrs. On cooling the product hydrochloride, 21.24 g, 88% was isolated by filtration, washed with acetone and air dried. The salt was dissolved in water (150 ml) and added to a solution of sodium acetate (7.2 g, 0.088 mole) in water (100 ml). The oil obtained was extracted into ethyl acetate, filtered to remove some insoluble material (0.4 g), dried and evaporated to dryness. The residue was crystallised from ethanol to give three crops of 2-(acetylmethylthio)benzimidazole (2), as colourless crystals, 15.0 g, 73%, mp. 112°–113° C. PMR was consistent with a tautomeric mixture of the open chain and ring closed forms.

$C_{10}H_{10}N_2OS$ Requires: C 58.2%, H 4.9%, N 13.6%, S 15.5%. Found: C 58.4%, H 5.2%, N 13.6%, S 14.5%.

(b) Preparation of 2,2-H-3-Methyl-1,3,4-thiadiazino[3,2-a]benzimidazole (3).

2-(Acetylmethylthio)benzimidazole (10.3 g, 50 mmole) was dissolved in a solution of potassium hydroxide (6.5 g, 115 mmole) in water (125 ml) and hydroxylamine O-sulphonic acid (tech. 6.2 g, 55 mmole) added in one portion with stirring at ambient temperature. The reagent dissolved immediately and after a few minutes a white precipitate was obtained. The mixture was stirred for 30 minutes and the product filtered off, washed and dried, 9.6 g, 95%. This was essentially one component by TLC (2:1 ethyl acetate:petrol). A sample was recrystallised from aqueous ethanol for characterisation, mp. 144°–146° C. Spectroscopic data was consistent for (3).

$C_{10}H_9N_3S$ Requires: C 59.1%, H 4.5%, N 20.7%, S 15.8%. Found: C 59.1%, H 4.7%, N 20.5%, S 15.5%.

(c) Preparation of 4-Acetyl-3-acetylthio-2-methylpyrazolo[1,5-a]benzimidazole (5)

2,2-H-3-Methyl-1,3,4-thiadiazino[3,2-a]benzimidazole (2.0 g, 10 mmole) was added to a mixture of toluene (20 ml) and acetic anhydride (5 ml) and heated to reflux for 24 hr. After 6 hr TLC (ethyl acetate) indicated approximately 40–50% conversion to a single product which only marginally increased with time. A further aliquot of acetic anhydride (5 ml) was added and heating continued for a total 80 hrs (followed by TLC). After this time TLC indicated a 80–90% conversion and a beige solid began to crystallise from the mixture. On cooling the mass of crystals were filtered off, washed with a little acetic acid and air dried, 2.6 g, 91%, mp. 191°–193° C. Spectroscopic data was consistent with (5).

$C_{14}H_{13}N_3O_2S$ Requires: C 58.5%, H 4.6%, N 14.6%, S 11.2%. Found: C 58.5%, H 4.7%, N 14.5%, S 11.3%.

(d) Preparation of 2-Methylpyrazolo[1,5-a]benzimidazole (6).

4-Acetyl-3-acetylthio-2-methylpyrazolo[1,5-a]benzimidazole (2.0 g, 6.97 mmole) was added to a mixture of concentrated hydrochloric acid (5 ml) and ethanol (30 ml) and refluxed for 5 hr. A yellow solid precipitated during the heating period and was filtered off after cooling, 0.9 g. This was a mixture of several components, none of them being the required product, and was discarded. The ethanolic solution was poured into a solution of sodium bicarbonate (excess) in water (300 ml) and the white solid filtered off, washed and dried, 0.7 g, 61%, mp. 250°–252° C. IR and TLC (+ Dox spray test) comparison with authentic (6) showed the samples to be identical.

EXAMPLE 2

The Ring Contraction Route (a) Preparation of 1,2-Diaminobenzimidazole (8).

Hydroxylamine O-sulphonic acid (tech. 23.25 g, 205 mmol) was added to a stirred solution of 2-aminobenzimidazole (25 g, 187.5 mmol) dissolved in water (600 ml) containing potassium hydroxide (24.6 g, 438 mmol) at 23° C. After a few moments a white solid began to precipitate. The mixture was stirred for 30 mins and the product collected by filtration, washed with water and dried in air at ambient temperature, 10.75 g. On standing overnight a second crop, 5.8 g was obtained. The total yield of product was 16.55 g, 60%, mp. 252°–254° C., (lit. 255°–259° C.). Spectroscopic analysis was consistent with the product but indicated a small amount of the starting material was also present. This was used without further purification (note 1).

Note 1: The product can be crystallised from ethanol.

$C_7H_8N_4$ Requires: C 56.7%, H 5.4%, N 37.8%. Found: C 58.1%, H 5.4%, N 36.5%.

(b) Preparation of 3H-2-Methyl-1,2,4-triazepino[2,3-a]benzimidazole-4(5H)-one (9)

1,2-Diaminobenzimidazole (3.0 g, 20 mmol) was added to a mixture of xylene (25 ml), ethyl acetoacetate (5.2 g, 40 mmol) and acetic acid (1.5 ml) and heated at 110° C. for 2 hr and then refluxed for a further 1 hr. After cooling to room temperature the precipitate was filtered off washed with toluene and dried in air to give pure (9), 2.5 g, 58%. Spectroscopic analysis was consistent with the product.

$C_{11}H_{10}N_4O$ Requires: C 61.7%, H 4.7%, N 26.15%. Found: C 61.5%, H 4.8%, N 26.1%.

c) Reaction of Triazepinone (9) with Acetic Anhydride

Triazepinone (9) (1.0 g, 4.67 mmol) was added to acetic anhydride (5 ml) and heated at reflux. The reaction was followed by thin layer chromatography, (1:1 ethyl acetate: 60°–80° C. petroleum ether), and indicated that two products (Rf=0.1 and 0.8, SM=0.15) were being formed. After heating for 4 hr the reaction was complete and the solution was allowed to cool to room temperature overnight. The mass of fine needles that were formed were filtered off, washed with a little acetic acid and dried in air, 0.65 g. Recrystallisation from acetic acid gave a pure sample of product 1, (Rf=0.8), identified as 5-H-2-Methyl-3-acetyl-4-acetoxy-1,2,4-triazepino[2,3-a]benzimidazole (10), mp. 218°–220° C. The yield of product 1 was 0.65 g, 47%.

Product 1; $C_{15}H_{14}N_4O_3$ Requires: C 60.4%, H 4.7%, N 18.8%. Found: C 59.9%, H 4.8%, N 18.5%.

The reaction filtrate, containing product 2, was poured into stirred water (75 ml) and the buff solid isolated by filtration, washed with water and dried in air. This was shown, by spectroscopic analysis, to be almost pure 2-methyl-4-acetylpyrazolo[1,5-a]benzimidazole (11), mp. 158°–160° C., 0.3 g, 35%.

Product 2; $C_{12}H_{11}N_3O$ Requires: C 67.6%, H 5.2%, N 19.7% Found: C 66.9%, H 5.2%, N 19.6%

(d) Preparation of 2-methylpyrazolo[1,5-a]benzimidazole (6)

2-Methyl-4-acetylpyrazolo[1,5-a]benzimidazole (11), (0.25 g, 1.17 mmol), was added to a mixture of concentrated hydrochloric acid (0.5 ml) in ethanol (5 ml) and heated to reflux for 20 minutes. The solution was cooled to room temperature and poured into a solution of sodium bicarbonate in water (30 ml) to afford a light tan solid which was filtered off, washed and dried, mp. 248°–252° C., 0.20 g, 99%. This was shown by comparative thin layer chromatography and infra-red analysis to be identical to an authentic sample of 2-methylpyrazolo-[1,5-a]benzimidazole (6).

EXAMPLE 3

The couplers described above were converted by conventional methods to the following ballasted couplers for photographic evaluation in an E6 process (well known development process for colour reversal processing e.g. Ektachrome).

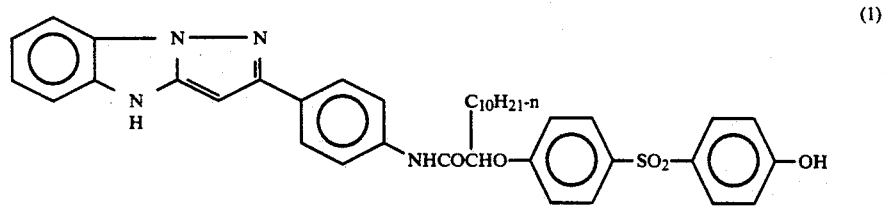

(1)

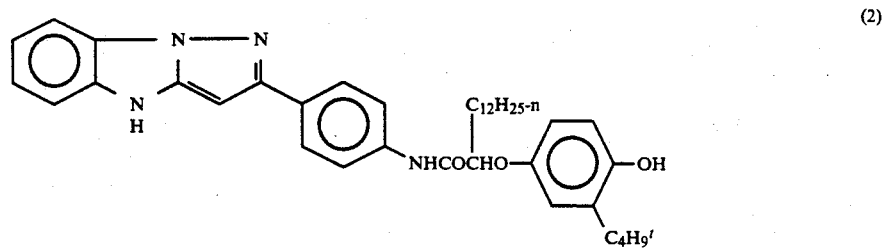

(2)

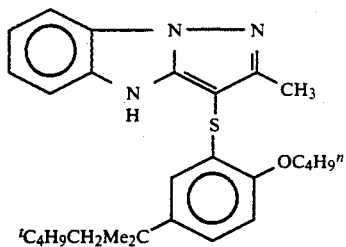

(3)

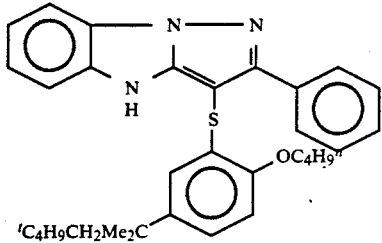

(4)

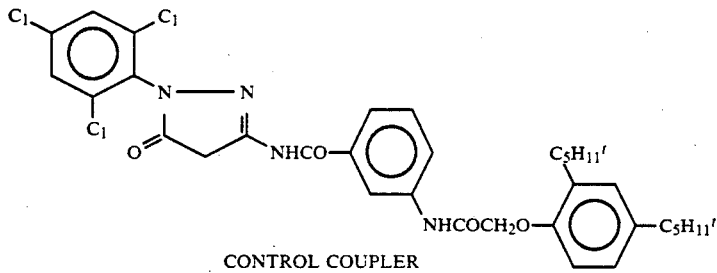

CONTROL COUPLER (5)

The couplers were incorporated into a photographic silver bromoiodide emulsion and coated in the following format:

| Gel Supercoat | Gelatin | 1.5 gm−2 |
|---|---|---|
| Emulsion | Silver bromoiodide | 1.6 gm−2 |
| Layer | Coupler | 1.04 mmolm−2 |
|  | Gelatin | 2.42 gm−2 |
|  | Bis(vinylsulphonyl)-methane (hardener) | 0.06 gm−2 |
| Support | Cellulose Acetate |  |

The couplers dispersion used contained 6% w/w gelatin, 0.8% coupler and coupler solvents in the ratio coupler:triphenyl phosphate:2-(2-butoxyethoxy)ethyl acetate 1.0:0.5:1.5.

Strips of the coated material were fogged through a step wedge and processed in a standard E6 process. Sensitometry was carried out on the strips to provide dye density curves from which Dmax and contrast (gamma) were measured. The dye hues (Lambda max) and half band width (HBW) were also measured.

| Coupler | Dmax | Dmin | Gamma | Lambda Max | HBW |
|---|---|---|---|---|---|
| (1) | 3.20 | 0.14 | −3.18 | 571 | 118 |
| (2) | 0.61 | 0.13 | — | 580 | 112 |
| (3) | 0.28 | 0.10 | — | 550 | 110 |
| (4) | 1.09 | 0.10 | −0.58 | 569 | 112 |
| (5) Control | 1.46 | 0.09 | −1.14 | 549 | 92 |

I claim:

1. A method for the production of a pyrazolo (1,5-a) benzimidazole of the formula (A):

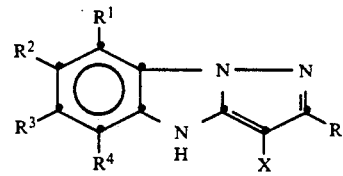

wherein

R is an alkyl or aryl group;

$R^1$–$R^4$ individually are R, H, halogen, or, COOR, CONHR, $SO_2$, $NO_2$, NHR, $NR_2$, or CN; and, X is hydrogen or a group releasable on coupling with an oxidized color photographic developer, wherein the method comprises reacting a 2-amino or 2-mercapto substituted benzimidazole to form a triazepinone or a thiadiazino derivative respectively, ring contracting said triazepinone or thiadiazino derivative to give the corresponding 2-methylpyrazolobenzimidazole product, and subsequently removing the substituents at the -3 or -4 positions to provide a compound of the formula (A).

2. A method according to claim 1 characterized in that R is methyl or phenyl and $R^1$ to $R^4$ are H.

3. A method according to claim 1 wherein R, $R^2$ and $R^3$ are methyl and $R^1$ and $R^4$ are hydrogen.

4. A method according to claim 1 wherein the 2-aminobenzimidazole is formed into a 1,2,4-triazepinone derivative being subsequently subjected to ring contracting of the sever-member ring to the pyrazole form.

5. A method according to claim 1 wherein the thiadiazinobenzimidazole derivative is subjected to ring contraction of the six-member ring to give the pyrazole form.

* * * * *

UNITED STATES PATENT AND TRADEMARK OFFICE
CERTIFICATE OF CORRECTION

PATENT NO. : 5,210,209
DATED : May 11, 1993
INVENTOR(S) : M.W. Crawley

It is certified that error appears in the above-indentified patent and that said Letters Patent is hereby corrected as shown below:

In Column 12, line 44, delete "or" and insert --OR--.

Signed and Sealed this

Eighth Day of March, 1994

Attest:

BRUCE LEHMAN

*Attesting Officer*   *Commissioner of Patents and Trademarks*